United States Patent
Shirwaiker et al.

(10) Patent No.: US 9,713,501 B2
(45) Date of Patent: Jul. 25, 2017

(54) ORBICULAR TISSUE EXPANDER

(71) Applicants: Wake Forest University Health Sciences, Winston-Salem, NC (US); North Carolina State University, Raleigh, NC (US)

(72) Inventors: Rohan A. Shirwaiker, Raleigh, NC (US); Caroline Elise Webster, Raleigh, NC (US); John D. Jackson, Clemmons, NC (US); Richard A. Wysk, Raleigh, NC (US); Sang Jin Lee, Winston-Salem, NC (US); Ola L. A. Harrysson, Raleigh, NC (US); James J. Yoo, Winston-Salem, NC (US); Anthony Atala, Winston-Salem, NC (US); Paul H. Cohen, Raleigh, NC (US); Yuan-Shin Lee, Raleigh, NC (US); Peter M. Prim, Raleigh, NC (US); Molly F. Purser, Raleigh, NC (US); Katie L. Basinger, Raleigh, NC (US)

(73) Assignees: Wake Forest University Health Sciences, Winston-Salem, NC (US); North Carolina State University, Raleigh, NC (US)

( * ) Notice: Subject to any disclaimer, the term of this patent is extended or adjusted under 35 U.S.C. 154(b) by 272 days.

(21) Appl. No.: 14/325,908

(22) Filed: Jul. 8, 2014

(65) Prior Publication Data
US 2015/0018948 A1  Jan. 15, 2015

Related U.S. Application Data

(60) Provisional application No. 61/844,053, filed on Jul. 9, 2013.

(51) Int. Cl.
*A61B 17/322* (2006.01)
*A61B 19/00* (2006.01)
*A61B 90/00* (2016.01)

(52) U.S. Cl.
CPC .............. *A61B 19/24* (2013.01); *A61B 90/02* (2016.02); *A61B 17/322* (2013.01); *A61B 2017/3225* (2013.01)

(58) Field of Classification Search
CPC ..... A61B 19/24; A61B 90/02; A61B 2017/02; A61B 17/322; A61B 2017/3225
See application file for complete search history.

(56) References Cited

U.S. PATENT DOCUMENTS 4,823,815 A * 4/1989 Watson .................. A61B 90/02
128/897
5,686,303 A 11/1997 Korman
(Continued)

OTHER PUBLICATIONS

Dick JC. The tension and resistance to stretching of human skin and other membranes, with results from a series of normal and oedematous cases. J. Physiol. 1951; 112: 102-113.

*Primary Examiner* — Alexander Orkin
(74) *Attorney, Agent, or Firm* — Myers Bigel, P.A.

(57) ABSTRACT

Provided herein is a tissue stretching device configured for orbicular expansion of a tissue placed therein. Methods of use of the device to stretch a tissue as well as for culturing organized tissues are also provided. Stretched and/or cultured tissues produced by these processes are also provided, as well as methods making use of the same.

20 Claims, 14 Drawing Sheets

(56) References Cited

U.S. PATENT DOCUMENTS

| | | | |
|---|---|---|---|
| 5,914,264 A | 6/1999 | Korman | |
| 6,668,836 B1 | 12/2003 | Greenburg et al. | |
| 6,733,537 B1 | 5/2004 | Fields et al. | |
| 2005/0101972 A1* | 5/2005 | Bhatavadekar | A61B 17/322 606/131 |
| 2008/0234602 A1* | 9/2008 | Oostman | A61B 10/0266 600/564 |
| 2011/0172683 A1 | 7/2011 | Yoo et al. | |
| 2012/0035620 A1* | 2/2012 | Sabir | A61B 17/322 606/132 |

\* cited by examiner

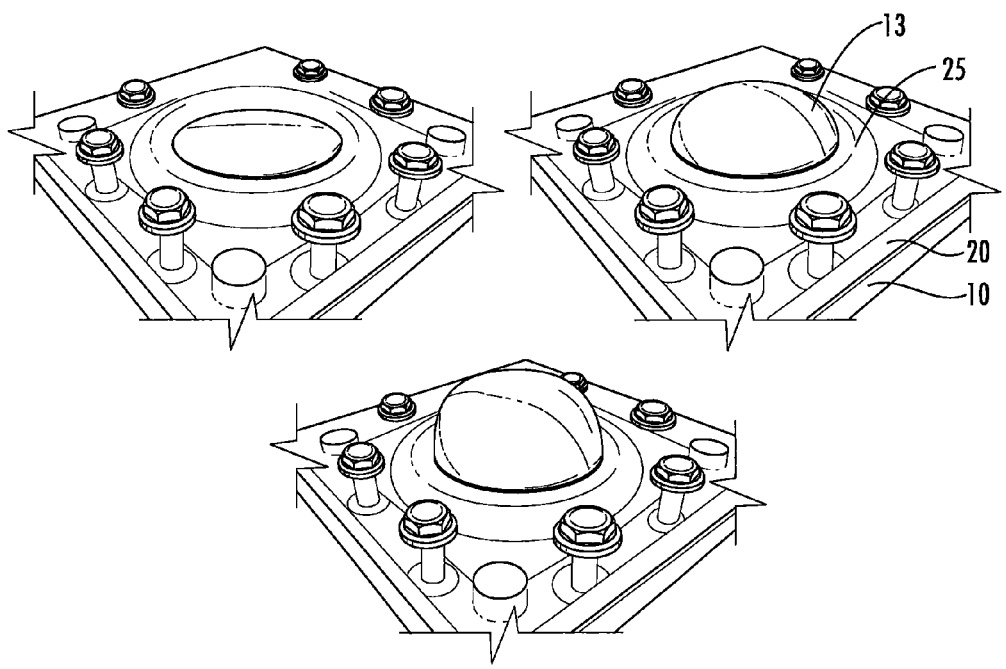
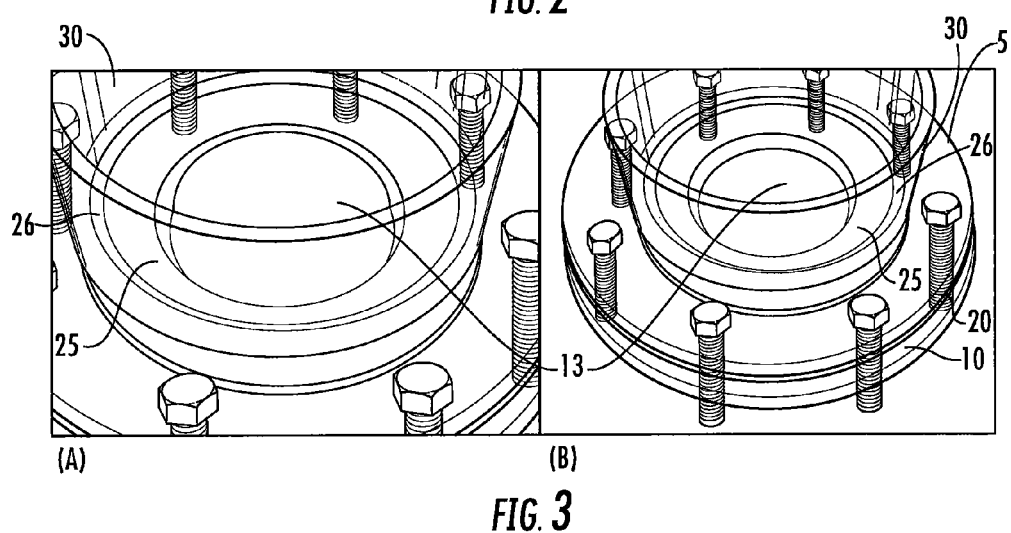
FIG. 2
FIG. 3

ORBICULAR TISSUE EXPANDER

STATEMENT OF GOVERNMENT SUPPORT

This work was supported by grant no. 1125872 from the National Science Foundation. The U.S. Government has certain rights in this invention.

BACKGROUND

There are several problems with using current split-thickness autologous skin grafting, particularly for large area burns. One of these is that it is often very painful for the patient. For large area burns, large pieces of skin are removed from the donor site and transplanted onto the affected area. The donor site must then heal, and cosmetic problems are increased because of scarring. In addition, there is a limited amount of skin harvests that can be taken from the same area, and there may not be enough uninjured skin to cover the injured site.

To treat patients with severe burns, smaller skin grafts can be harvested from healthy places on the body, expanded to a larger area in vitro, and then transplanted to a burned area of the body. However, an effective and efficient skin expansion bioreactor approach still remains a challenge. Current prototype skin expansion bioreactors have been reported to cause tissue tearing due to uneven loading, gripping method, stress concentration, and other factors intrinsic to the tissue properties. More effective in vitro expansion devices are needed.

BRIEF SUMMARY OF EMBODIMENTS

Provided herein is a tissue stretching device configured for orbicular expansion of a tissue (e.g., skin or muscle tissue). In some embodiments, the device comprises: a bottom solid support comprising a fluid chamber therein, said fluid chamber having a fluid inlet and fluid outlet; an expandable membrane attached to said bottom solid support (e.g., removably attached or permanently attached) and configured to be in fluid communication with a fluid (e.g., a liquid such as water or saline) in said chamber, wherein said expandable membrane is configured to undergo orbicular expansion in the presence of fluid pressure in said chamber; a top solid support having an opening therein (e.g., a circular, substantially circular, oval, or substantially oval opening); a perimeter member further defining said opening of said top solid support and configured to hold the tissue onto the expandable membrane during the expansion; wherein the bottom solid support is configured to attach the top solid support (e.g., with attachment members (e.g., bolts, clamps, hinges, etc.)), wherein said expandable membrane and said perimeter member are situated between said bottom solid support and said top solid support.

In some embodiments, the perimeter member comprises a friction surface to hold the tissue onto the expandable membrane during the expansion. In some embodiments, the perimeter member comprises protrusions sized to puncture and/or penetrate the tissue to hold the tissue onto the expandable membrane during the expansion.

In some embodiments, the expandable membrane comprises an expandable polymer (e.g., rubber such as silicone rubber).

In some embodiments, the top solid support further comprises a chamber configured to hold media in fluid communication with a tissue being stretched in said device.

In some embodiments, the perimeter member comprises one or more O-rings to provide a fluid seal.

In some embodiments, the opening of said perimeter member is circular and has a diameter of from 0.5, 1, 2, 3, or 5, to 8, 10, 15 or 20 centimeters.

In some embodiments, the friction surface of said perimeter member comprises a rough pattern.

In some embodiments, the device further comprises a pressure detector and/or controller operatively associated with the fluid of said fluid chamber.

Also provided is a method of orbicularly stretching a tissue comprising: attaching a tissue (e.g., skin or muscle tissue) into the device as taught herein; and stretching the tissue with the device, to thereby orbicularly stretch the tissue.

In some embodiments, the tissue is skin tissue comprising an epidermal tissue layer and a dermal tissue layer. In some embodiments, the attaching is carried out by placing the skin tissue with the epidermal surface in direct contact with said expandable membrane, and overlaying said tissue with the friction surface of said perimeter member on the dermal surface.

Also provided is the use of an orbicularly stretched tissue produced by a method taught herein, e.g., for tissue reconstruction or plastic surgery.

Further provided is a method of treating a skin wound on a subject in need thereof, comprising: providing a skin tissue harvested from a donor; stretching the skin tissue with a device taught herein to form an orbicularly stretched skin tissue; and then, grafting the orbicularly stretched skin tissue onto said subject, to thereby treat the skin wound.

In some embodiments, the skin tissue is allogeneic. In some embodiments, the skin tissue is autologous.

In some embodiments, the stretching is carried out over a time of from 1, 2, 3, 4 or 5 hours, to 2, 4 or 5 days, or even 1 or 2 weeks.

In some embodiments, the stretching is carried out by applying continuous or periodic pressure onto said tissue.

The foregoing and other objects and aspects of the present invention are explained in greater detail in the drawings herein and the specification set forth below.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 2 shows photographs of side perspective views of the assembled device according to some embodiment in which orbicular expansion of the tissue is progressing.

FIG. 3 shows photographs of the assembled device according to some embodiments in which a media reservoir is provided on the top solid support, wherein media may be provided in fluid contact with the dermal surface of stretching skin.

DETAILED DESCRIPTION OF EMBODIMENTS

Figure 1:
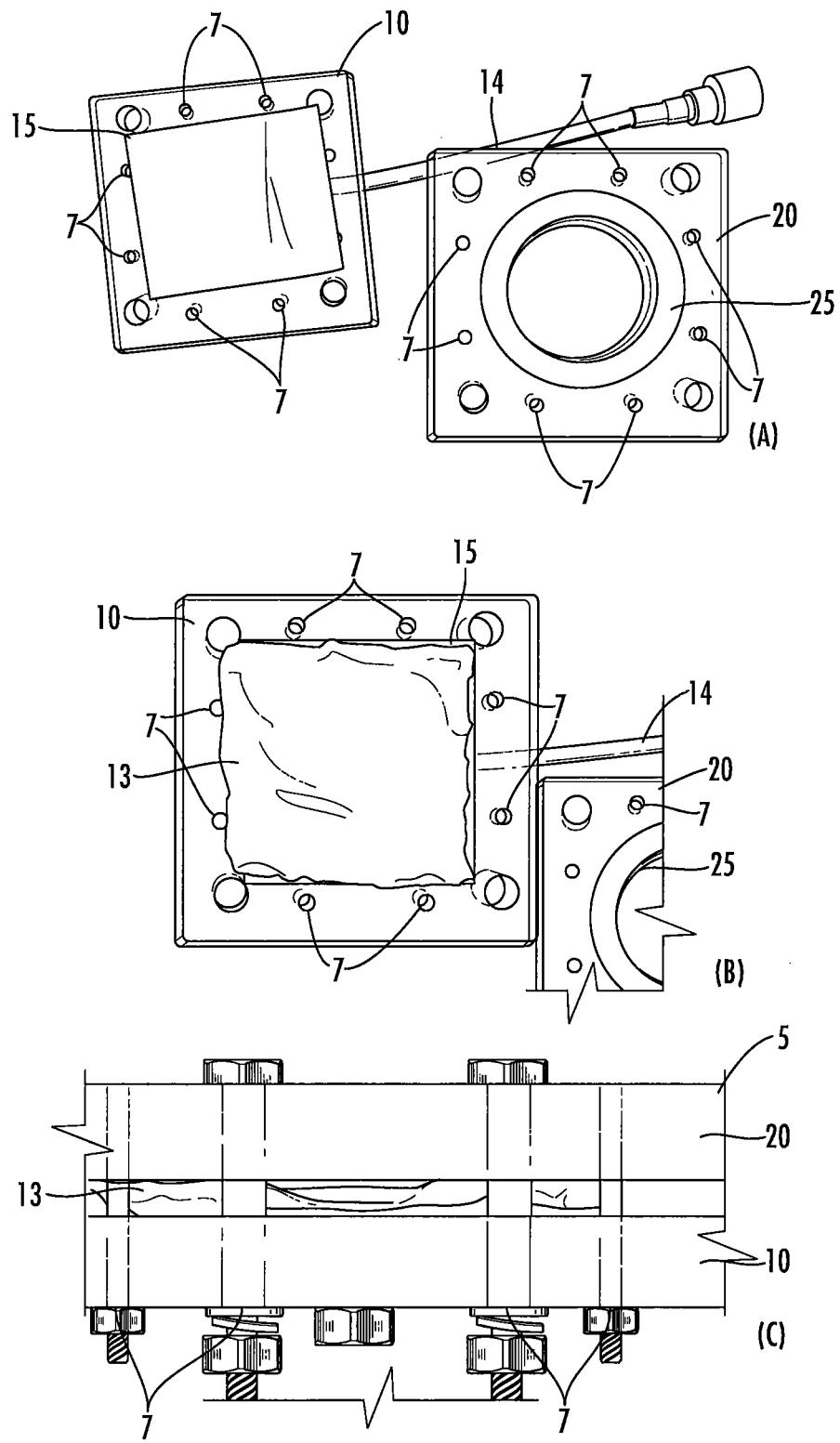
FIG. 1 shows photographic views of portions of the device according to some embodiments. Panel (A) is a top view of a bottom solid support with an expandable membrane situated thereon (left), and a bottom view of a top solid support with an perimeter member situated thereon (right), Panel (B) is a top view of the bottom solid support from (A) with tissue applied onto the flexible membrane. Panel (C) is a side view of the assembled device with the tissue therein.

Provided herein and further described below are devices and methods useful for the culturing, conditioning and/or stretching of tissues. Tissues that may be conditioned/stretched/cultured include intact tissues harvested from a suitable donor, as well as cells harvested from a donor and seeded onto a suitable support.

The disclosures of all United States patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. Furthermore, the terms "about," "approximately" and "substantially" as used herein when referring to a measurable value such as a length, volume, amount, dose, time, temperature, and the like, is meant to encompass variations of 20%, 10%, 5%, 1%, 0.5%, or even 0.1% of the specified number or measurement. Also, as used herein, "and/or" or "/" refers to and encompasses any and all possible combinations of one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly-used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for the sake of brevity and/or clarity.

Like numbers refer to like elements throughout. In the figures, the thickness of certain lines, layers, components, elements or features may be exaggerated for clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Provided herein according to some embodiments is a fluid pressure-based orbicular expansion device useful to induce permanent deformation (expansion) in skin or other tissues/tissue constructs. The proposed bioreactor device design in some embodiments applies a more evenly-distributed pressure on the tissue and reduces tearing around points of attachment to the device. This is in contrast to current biaxial skin stretching techniques, in which forces are applied to the tissue in two directions, which directions may not be aligned with the collagen fiber orientation. By using a more natural inflated pressure approach, the tissue can grow more freely and evenly and with less dependency on the collagen orientation.

"Fluid" as used herein refers to a substance that has no fixed shape and yields or flows easily in response to external pressure. In some embodiments, the fluid is a liquid such as water. In other embodiments, the fluid is a gas such as air or nitrogen.

As used herein, "orbicular" expansion of the tissue means expansion into a three-dimensional rounded convex or globular shape, such as a dome or semi-spherical shape.

In some embodiments, at least some of the forces transferred to the tissue to accomplish orbicular expansion of the tissue are provided by an expandable membrane situated directly under the tissue in the device and in direct contact therewith. As described in more detail below, the membrane and tissue situated thereupon may be expanded upon injecting a fluid into a chamber in fluid communication with the expandable membrane. In some embodiments, the membrane is biocompatible. In some embodiments, the membrane may be an expandable polymer such as rubber (e.g., silicone rubber) or another expandable elastomeric material. In some embodiments, the membrane may further comprise a non-stick layer on the side in direct contact with the tissue, such as a non-stick polymeric layer, or an ointment, gel or hydrogel. See also U.S. Pat. No. 4,666,447 to Smith et al. and U.S. Pat. No. 4,984,585 to Austad. In further embodiments, the expandable membrane may be a membrane that expands from a folded to an unfolded configuration to thereby increase the surface area.

As further described below, according to some embodiments, tissue may be attached to the device using a perimeter member having a friction surface. The friction surface of the perimeter member directly contacts at least one surface of the tissue and provides a friction-based attachment into the device. In preferred embodiments the perimeter member directly contacts one surface, and in some embodiments the contact is all along the mating interface of the friction surface and tissue. The friction surface in some embodiments may be patterned to provide the friction, for example, having a rough surface such as a knurl-like (i.e., cross-hatched) pattern, parallel ridges or concentric circles. In some embodiments the surface include pins and/or hooks, etc. See also U.S. Pat. No. 7,208,006 to Fleishmann.

The friction of the friction surface upon engagement with the tissue in the assembled device in some embodiments is sufficient to hold the tissue in place in the device during expansion, but does not significantly penetrate the tissue, thus reducing the concentration of stress at the outer edges of the tissue during expansion and allowing the tissue to fail at its weaker point(s). The friction of the friction surface in conjunction with the force applied from expansion of the expandable membrane according to some embodiments results in the tissue having a more evenly-distributed application of force, with forces applied to the middle of the tissue in addition to the edges of the tissue, thereby reducing tissue failures at the points of attachment during expansion. It should be noted that, while the forces may be distributed more equally, stresses may be unequal due to variation in graft thickness along the tissue.

In some embodiments, tissue may be attached to the device using a perimeter member having protrusions sized to puncture and/or penetrate the tissue. The protrusions may be used in addition to friction surface in some embodiments.

Figure 16:
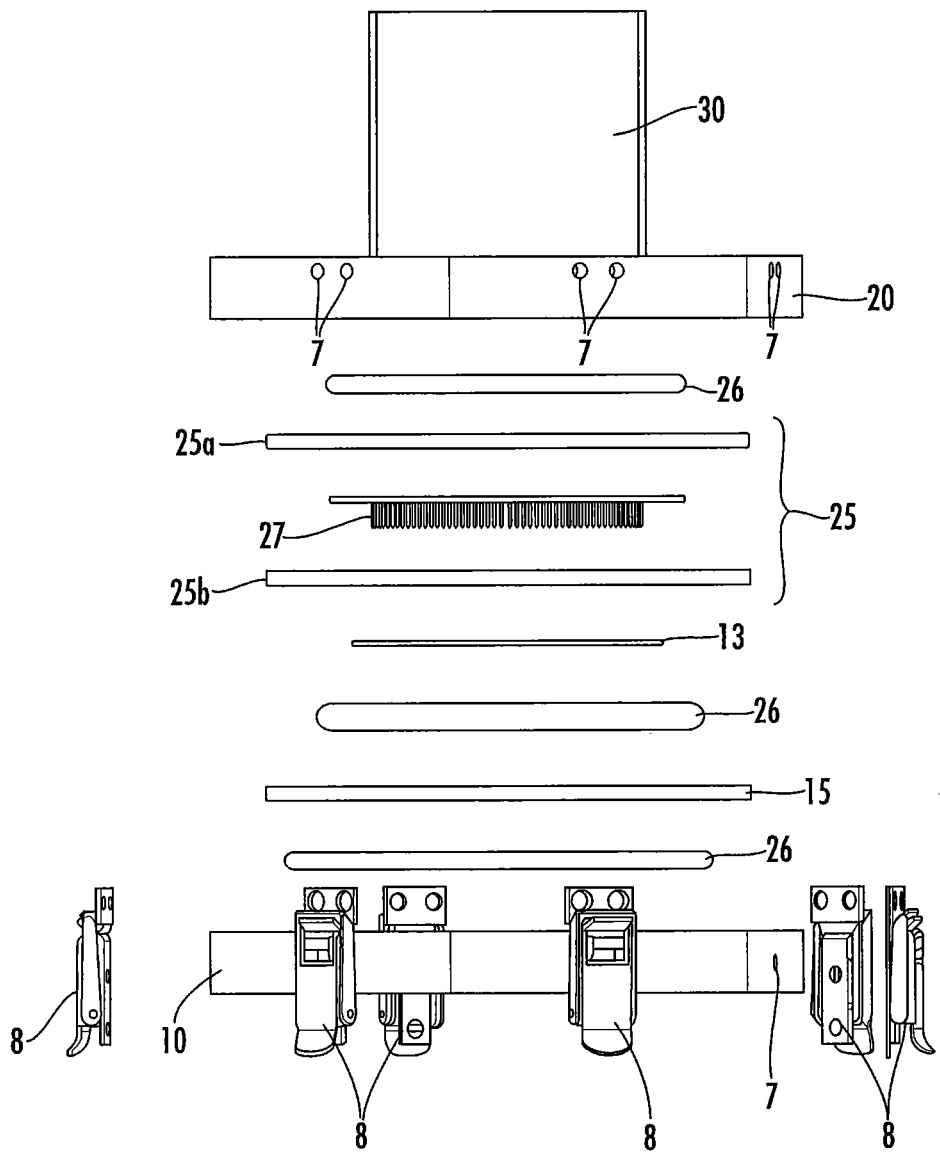
FIG. 16 presents an exploded side view of an orbicular expander device according to some embodiments.
Figure 17:
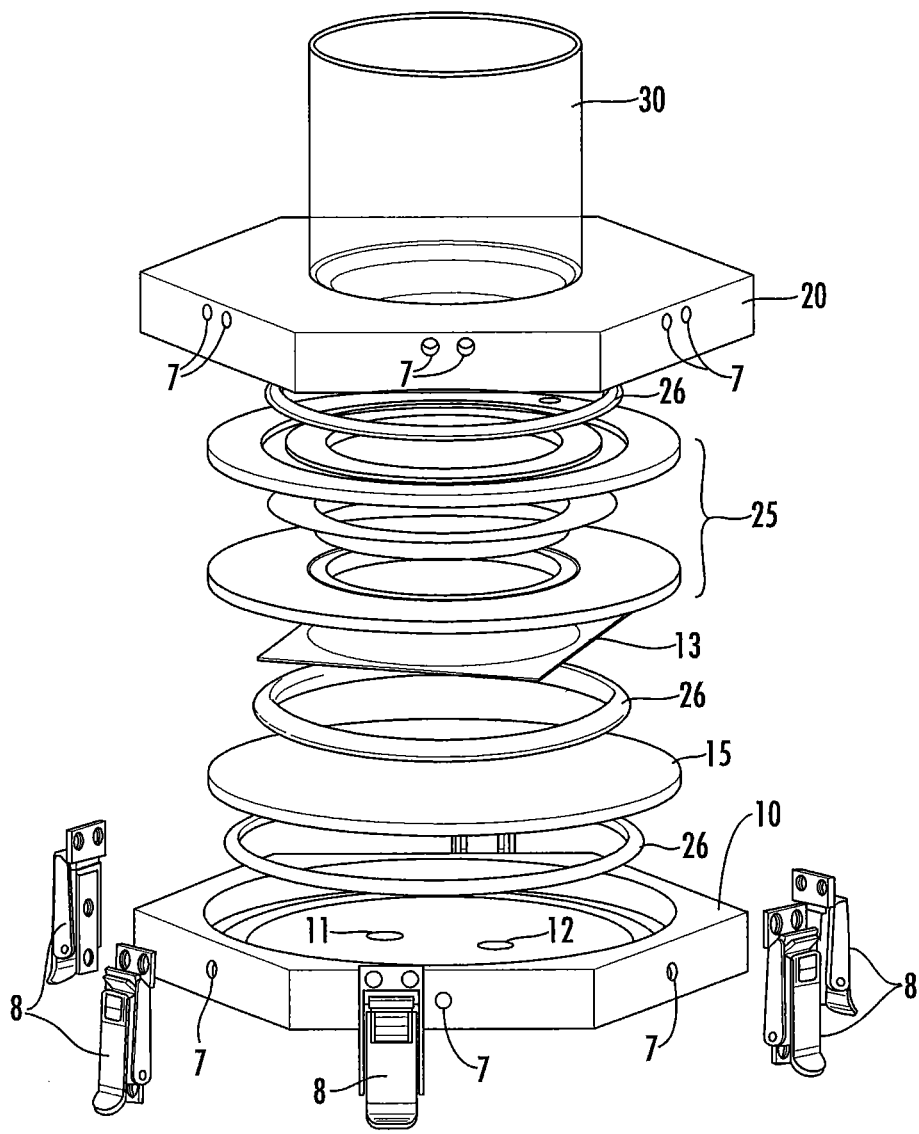
FIG. 17 presents an exploded perspective view of an orbicular expander device according to some embodiments, including the tissue to be stretched.

An exemplary embodiment of the protrusions as pins (27) can be seen in FIG. 16 and FIG. 17. In some embodiments, e.g., for use with skin tissue, the protrusions are pins having a diameter of from 0.01 mm to 1.0 mm, or from 0.1 mm to 0.9 mm, or from 0.25 mm to 0.75 mm. In some embodiments, the protrusions may be spaced at from 0.1 mm to 10 mm, or from 0.5 mm to 5 mm, or from 1 mm to 2 mm, measuring from the center of one protrusion to the center of an adjacent protrusion.

In some embodiments, the device is assembled to hold the top solid support onto the bottom solid support with a force at points of attachment (7) from 0.01 MPa to 1.0 MPa, or from 0.1 MPa to 0.9 MPa, or from 0.25 MPa to 0.75 MPa.

Expanded tissue produced as described herein may be used for treatment such as the replacement and/or reconstruction of damaged tissue in a patient. Such tissue may be grafted or implanted into the subject using procedures known in the art. Though the tissue is expanded herein in an orbicular manner, the stretched skin may thereafter be allowed to flatten and/or be molded to the form/part of the body it will be grafted upon.

"Treat" refers to any type of treatment that imparts a benefit to a subject, e.g., a patient afflicted with a trauma or disease, or otherwise desirous of a tissue graft. Treating includes actions taken and actions refrained from being taken for the purpose of improving the condition of the patient (e.g., the promotion of healing and/or formation of tissues on a patient in need thereof, the relief of one or more symptoms, etc.).

In some embodiments, treating includes tissue grafting as part of tissue replacement after a trauma (e.g., burn injury). In some embodiments, treating includes reconstructing skin tissue (e.g., where such tissue has been damaged or lost by injury or disease) by grafting or implanting tissues onto a subject in need thereof. In some embodiments, treating includes construction or augmentation of tissue as desired by a patient, e.g., for plastic surgery.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult and geriatric subjects.

Subjects may also include animal subjects, particularly vertebrate subjects, e.g., mammalian subject such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes.

The tissue to be stretched is preferably human for use in human recipients, but veterinary use is also encompassed by the invention, as noted above. Tissue scaffolds (e.g., decellularized tissues) may also be used, and may be seeded with cells, if desired. Tissues and/or cells seeded onto tissue scaffolds may be autologous (i.e., from the very subject to which they will be applied), syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic (i.e., from the subject to be treated) and isogeneic (i.e., a genetically identical but different subject, e.g., from an identical twin). Tissues and/or cells may be obtained from, e.g., a donor (either living or cadaveric) or derived from an established cell strain or cell line. For example, cells may be harvested from a donor using standard biopsy techniques known in the art. For allogeneic transplant into a patient, tissue as described herein may be matched or tissue-typed in accordance with known techniques, and/or the subject may be administered immune suppressive agents to combat tissue transplant rejection, also in accordance with known techniques.

In such a case where the grafting is not needed immediately, autologous tissue may be harvested and expanded in vitro for from 2, 3, 4, or 5 days to 7, 10, or 1 or 2 weeks before grafting. In other embodiments where the tissue is of more immediate need (e.g., severe burns), autologous tissue may be harvested and expanded in vitro from 24 or 48 hours, to 3, 4 or 5 days before grafting onto the patient.

In some embodiments, a segment of vertebrate tissue is obtained (e.g., skin tissue) and placed in an artificial cell growth medium containing sufficient nutrients to maintain growth of cells of the tissue segment. The tissue segment may then be subjected to stretching forces while bathed or submerged in the medium. In various embodiments of the invention, the stretching forces may be dynamic (e.g., cyclic) or static, orthogonal or radial. See also U.S. Pat. No. 6,364,908 to Ysebaert.

Expanded tissue produced as described herein may also be used in vitro, in the apparatus described herein or in a separate apparatus, to examine the pharmacological or toxicological properties of compounds of interest, for example, by adding the compound of interest to a culture medium in which the tissue is immersed, and examining the histological or mechanical properties of the tissue as compared to a control tissue without the presence of the compound.

In the following description of various embodiments of the invention, the invention is described in most cases as being practiced with a human tissue autograft. However, the invention is not so limited and can be used for both allografts (within the same species, but with the donor and recipient being different individuals) and xenografts (donor and recipient from different species). Additionally, the invention is not limited to preparation of human tissue, since it can be advantageously practiced to produce large amounts of normal tissue of various vertebrates, either for veterinary use as autografts or allografts, or for use in the production of xenografts (which would normally require suppression of the immune system of the recipient when the product tissue is used as a graft), since even the temporary protection against infection and sepsis provided by a xenograft may save the life of the recipient organism. For veterinary or xenograft use, the donor tissue can be obtained from any vertebrate, preferably one related as closely as possible to the recipient. Non-exclusive examples include tissue from humans, other primates, cattle and other domesticated bovines, pigs, hogs, cats, dogs, sheep, goats, birds, and reptiles.

A segment of vertebrate tissue (graft donor segment) may be obtained by any of the techniques normally available for this purpose, usually surgical excision or use of a dermatome (for split-thickness skin). If a dermatome (i.e., any plane-like device for removing skin from a subject) is used, the thickness of the layer should be selected to ensure that at least some of the dermal layer is present. This thickness will vary from species to species and even from location to location on the body of an individual. A typical setting for a dermatome used to prepare split-thickness human skin is about $^{12}/_{1000}$th of an inch (about 0.3 mm, or in a range of 0.2 mm to 0.5 mm). The skin segment is obtained so that both dermal and epidermal layers are present in the detached segment. The dermal layer can be either complete (full-thickness skin) or incomplete (split-thickness skin), but it is preferred that at least some of the dermal layer be present.

Full-thickness skin segments are typically obtained by surgical excision, while split-layer skin segments are typically obtained by a dermatome. Both of these techniques, as well as other general techniques in the field of skin grafting, are described in Chapter 1 (pp. 1-90) of Grabb and Smith, Plastic Surgery, Little Brown & Company, Boston, Mass., USA, 4th Ed. (1991), James W. Smith and Sherrell J. Aston, eds. The detached skin is normally transferred directly to a culture medium, and in most cases is not allowed to dry out before being positioned in the medium.

The shape of the detached skin segment is not material to the practice of the invention, but certain shapes may be better suited to individual specific apparatus variations described here (e.g., square, rectangular, substantially square or substantially rectangular, circular, oval, substantially circular or substantially oval, etc.). See also U.S. Pat. No. 5,914,264 to Korman.

The size of the donor tissue segment is generally selected for the convenience of use with the apparatus in which it will be stretched and may also vary depending on the availability of donor skin tissue of the same type as that being replaced. Typical human skin segments are from 1×1 cm to 10×30 cm, but can vary significantly depending on the availability of donor skin. For ease of handling in surgical skin grafting, segments ranging in size from about 4×4 cm or 5×5 cm to about 10×10 cm or 15×15 cm may be used; however, other suitable sizes may be used.

Preparation and use of artificial cell-growth media containing sufficient nutrients to maintain growth of cells of a skin segment are well-established techniques and need not be described here in detail. Such media are also referred to as nutrient media or tissue culture media. Whether any given medium will be satisfactory (if not already known) can easily be determined experimentally using the procedures for skin growth known in the art. Many such media are commercially available, such as Dulbecco's modified Eagle's medium (DMEM) with 10% added fetal calf serum. Other suitable media include basal medium (Eagle) with Hanks's BSS (85%) supplemented with calf serum (15%) and Ham's F12 medium (90%) supplemented with fetal bovine serum (10%). When serum is used to supplement an artificial medium, in some embodiments fetal serum is preferred, especially fetal serum from the same species as the recipient of the graft. When this is not possible or ethically desirable, the recipient's own serum can be used. For a number of media that can be used to grow skin tissue, see, for example, the media formulations section of any volume of the American Type Culture Collection publication entitled Catalogue of Cell Lines & Hybridomas (e.g., 5th edition, 1985, pages 265-273). This ATCC publication also contains information (in connection with specific skin-derived cell lines) on which media are best for use with tissue or cell cultures derived from skin.

As illustrated in FIG. 1, in some embodiments a device (5) includes a bottom solid support (10) and a top solid support (20). The bottom solid support (10) is configured to receive an expandable membrane (15) therein, under which a fluid may be delivered via a fluid connector (14). The top solid support (20) defines a substantially circular opening in its center in which tissue (13) may expand, with the inner edge of the top solid support coextensive or overlapping with the inner edge of a perimeter member (25). The inner edge of the perimeter member (25) further defines the substantially circular opening in its center in which tissue (13) may expand. Points of attachment (7) provided placed for bolts or other attachment members (e.g., clamps, etc.) to hold the top solid support (20) onto the bottom solid support (10) and secure the tissue (13) and perimeter member (25) thereon during expansion (FIG. 2).

The perimeter member (25) may be provided as a separate piece and may be removably attached to the device, as illustrated in some embodiments herein. Alternatively, the perimeter member (25) may be attached to or directly integrated with the top solid support (20) without departing from the teachings of the present invention.

The expandable membrane (15) may be provided as a separate piece and may be removably attached to the device, or may be attached to or directly integrated with the bottom solid support (10).

As show in FIG. 3, in some embodiments, the top solid support (20) includes a chamber (30) configured to hold media, and the media is in fluid contact with at least a portion of the tissue. A top (not shown) may also be provided, that is configured to cover and/or seal the chamber (30). The chamber (30) may further include a media inlet and media outlet to allow media change/replenishment without the need to open the chamber (not shown). The media inlet may in some embodiments be in fluid connection with a media reservoir (not shown) which is configured to hold fresh, sterile media.

A gas inlet (not shown) may also be provided on the chamber (30). Any suitable gas, such as air or an air/5% $CO_2$ mixture, may be used in order to promote tissue growth. The gas inlet may be operatively connected to a device for metering the gas, as well as a HEPA filter to remove contaminates (not shown). A gas outlet may also be provided on the chamber (not shown).

Figure 4:
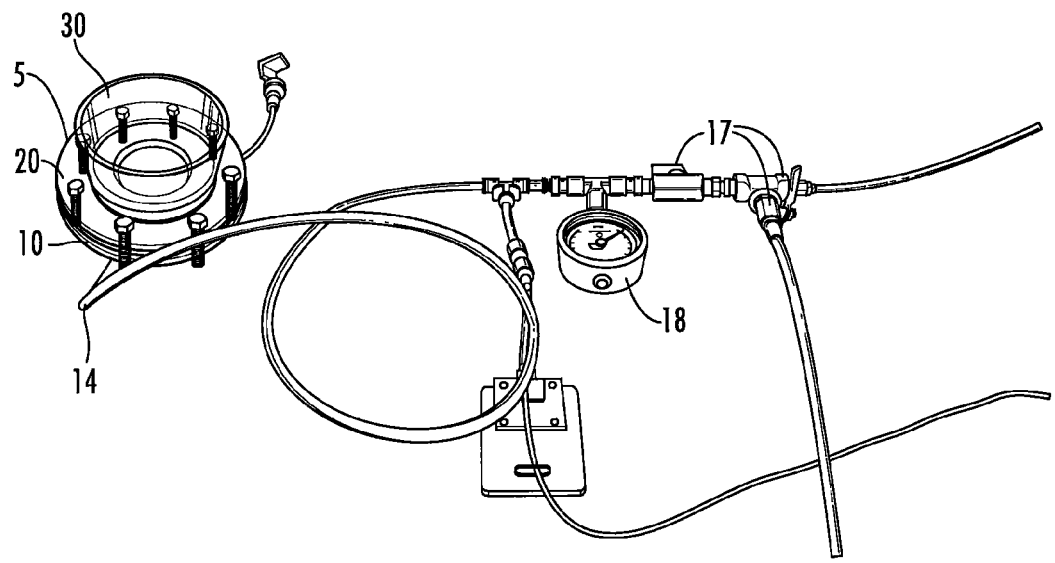
FIG. 4 shows a photograph of a side perspective view of the assembled device according to some embodiments and shows tubing connected to the bottom solid support, and connection of a pressure gauge and valves to control the pressure exerted by the flexible membrane.

As illustrated in FIG. 4, a pressure gauge (18) or other means for measuring the amount of fluid pressure applied may be provided on the fluid connector (14), as well as valves (17) to regulate the fluid pressure/volume.

Figure 5:
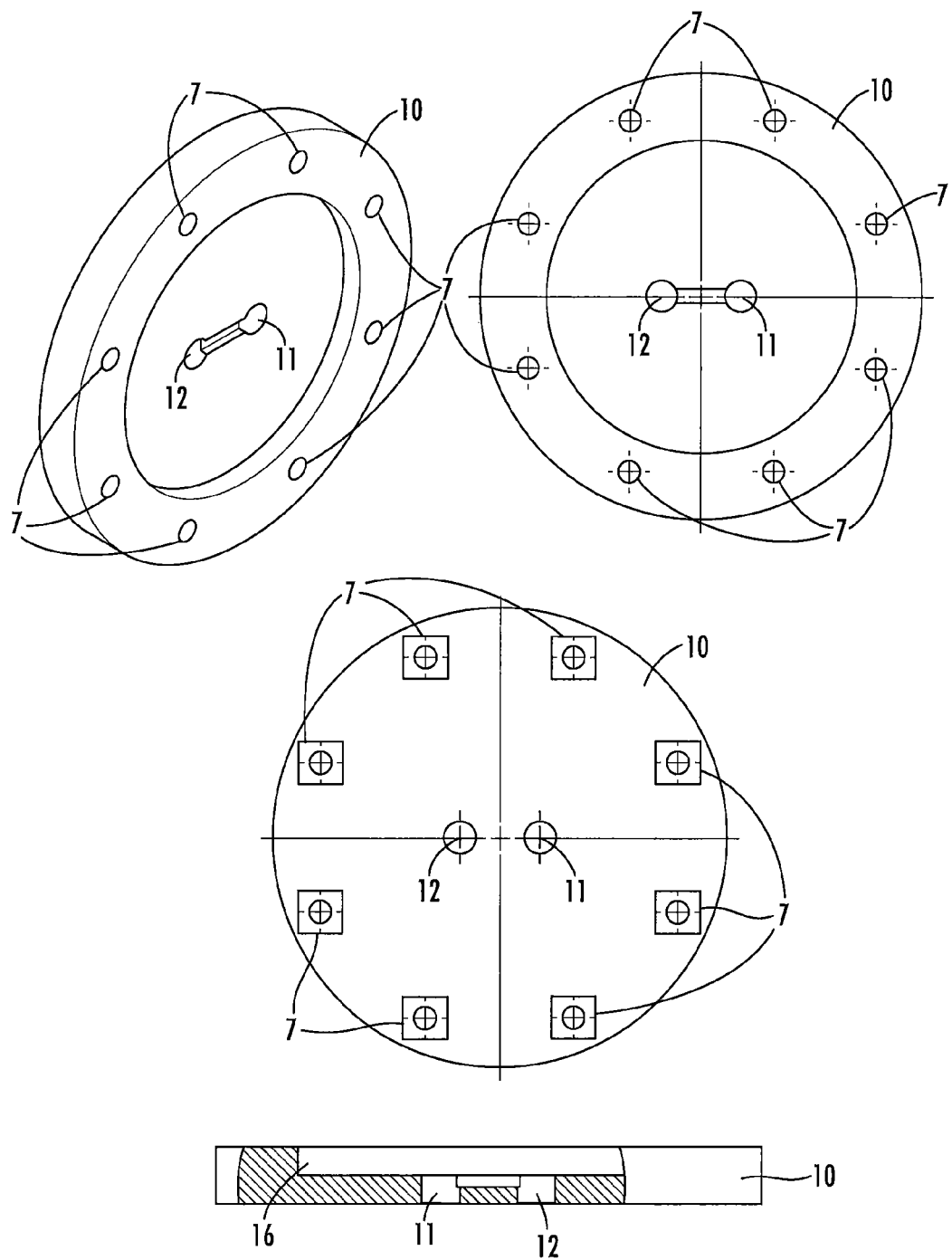
FIG. 5 is a schematic drawing of a bottom solid support according to some embodiments.

As illustrated in FIG. 5, the bottom solid support (10) according to some embodiments has a fluid inlet (11) and fluid outlet (12), each connecting to a fluid chamber (16). After bleeding the fluid chamber (16), the fluid outlet (12) may be closed to prevent fluid flow while the fluid flows into the fluid inlet (11), resulting in an increase in the volume/pressure of the fluid in the bottom solid support (10) under the expandable membrane (15). As shown in the top left panel, the bottom solid support (10) may be configured on the top surface thereof to receive the expandable membrane (15), which forms the top of the fluid chamber (16).

Figure 6:
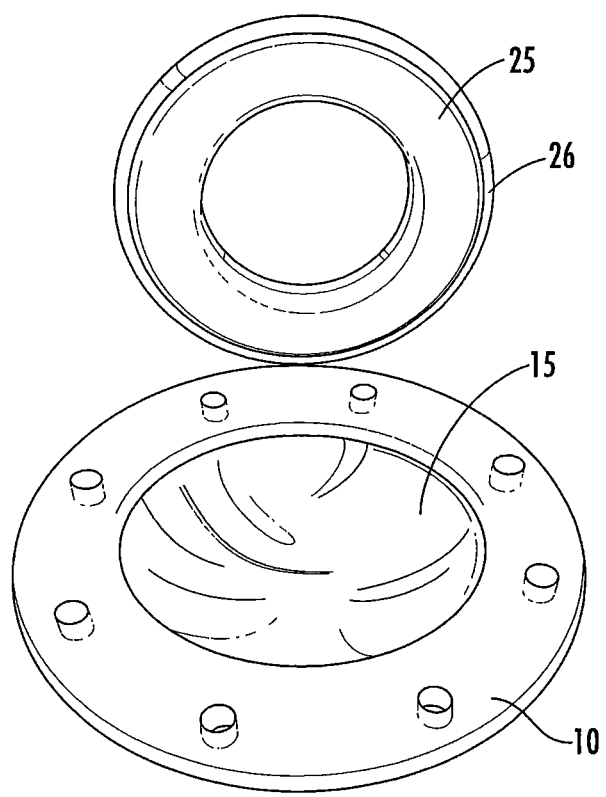
FIG. 6 is a photograph of a top perspective view of the bottom solid support according to some embodiments. The bottom solid support of the embodiment is configured to receive a circular expandable membrane, as shown. Tissue is sandwiched between the membrane and the perimeter member (shown held above the bottom solid support), with the friction surface of the perimeter member placed in direct contact with the tissue and holding the tissue in place during expansion. An O-ring on the perimeter member provides a liquid seal between the top and bottom portions of the device.

Placement of the expandable membrane (15) into the bottom solid support (10) according to some embodiments is illustrated in FIG. 6. The expandable membrane (15) may include a non-stick coating or cover to allow movement of the tissue (13) relative to the expandable membrane (15) during the orbicular expansion. After placing the tissue (13) onto the expandable membrane (15), the perimeter member (25), which further defines the substantially circular opening therein, is placed onto the tissue, with a friction surface in direct contact with the tissue (13). For skin tissue having an epidermal and dermal layer, it is preferred that the epidermal surface is placed onto the expandable membrane (15), while the dermal surface is faced upward and in contact with the friction surface of the perimeter member (25).

Figure 7:
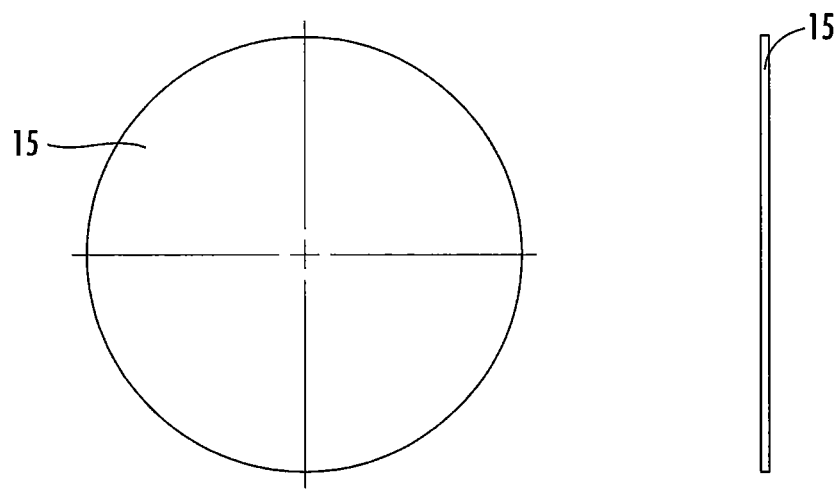
FIG. 7 is a schematic drawing of the top view and side view of a round-shaped expandable membrane according to some embodiments.

FIG. 7 illustrates a circular shape of the expandable membrane (15) according to some embodiments; however, the expandable membrane (15) may also be other shapes, such as square (as shown in FIG. 1).

Figure 8:
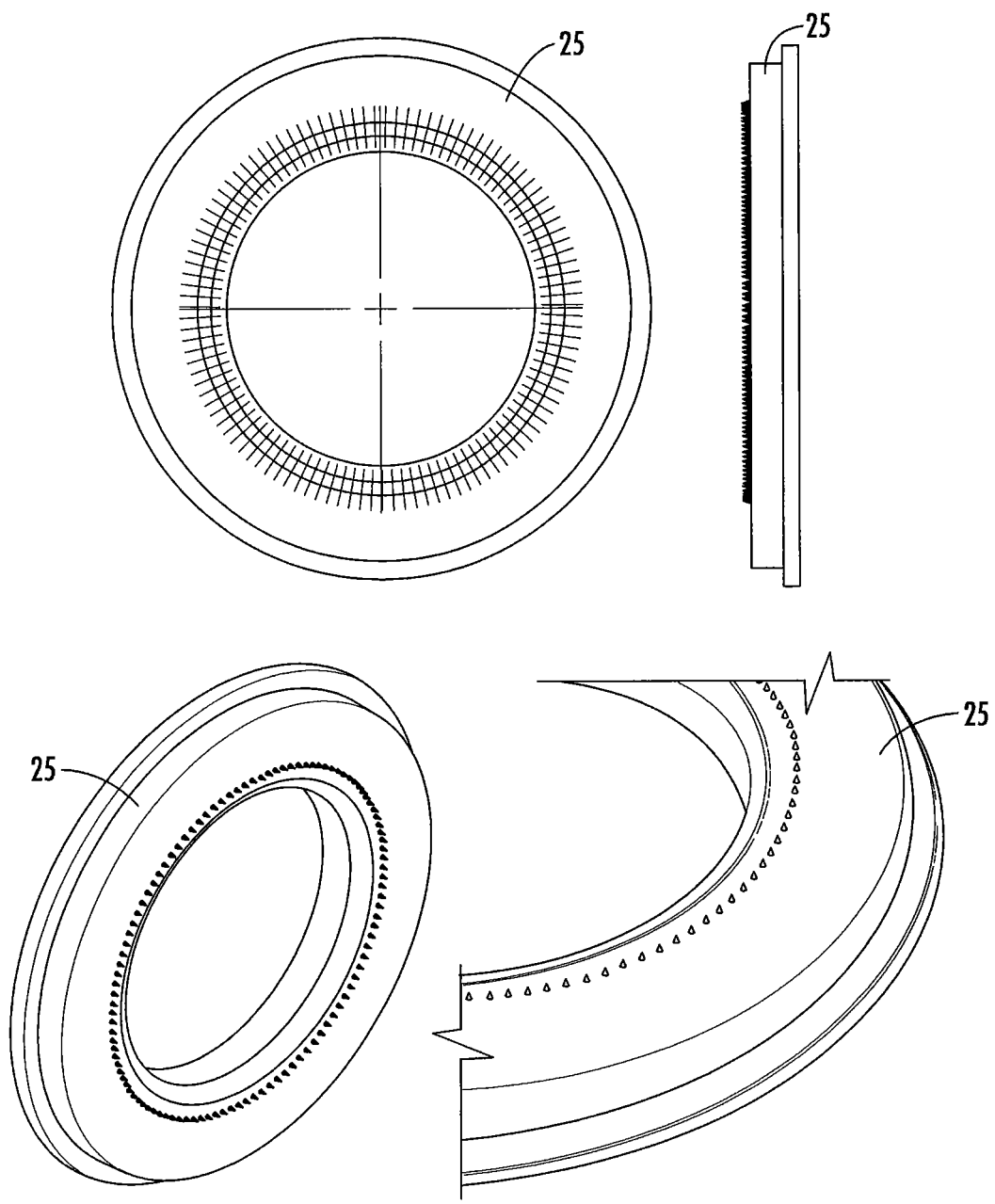
FIG. 8 shows schematic drawings and a photograph of a round-shaped perimeter member according to some embodiments having a pin friction surface thereon. The outer edge of the perimeter member may have a ridge configured to accept an O-ring as a liquid seal.
Figure 9:
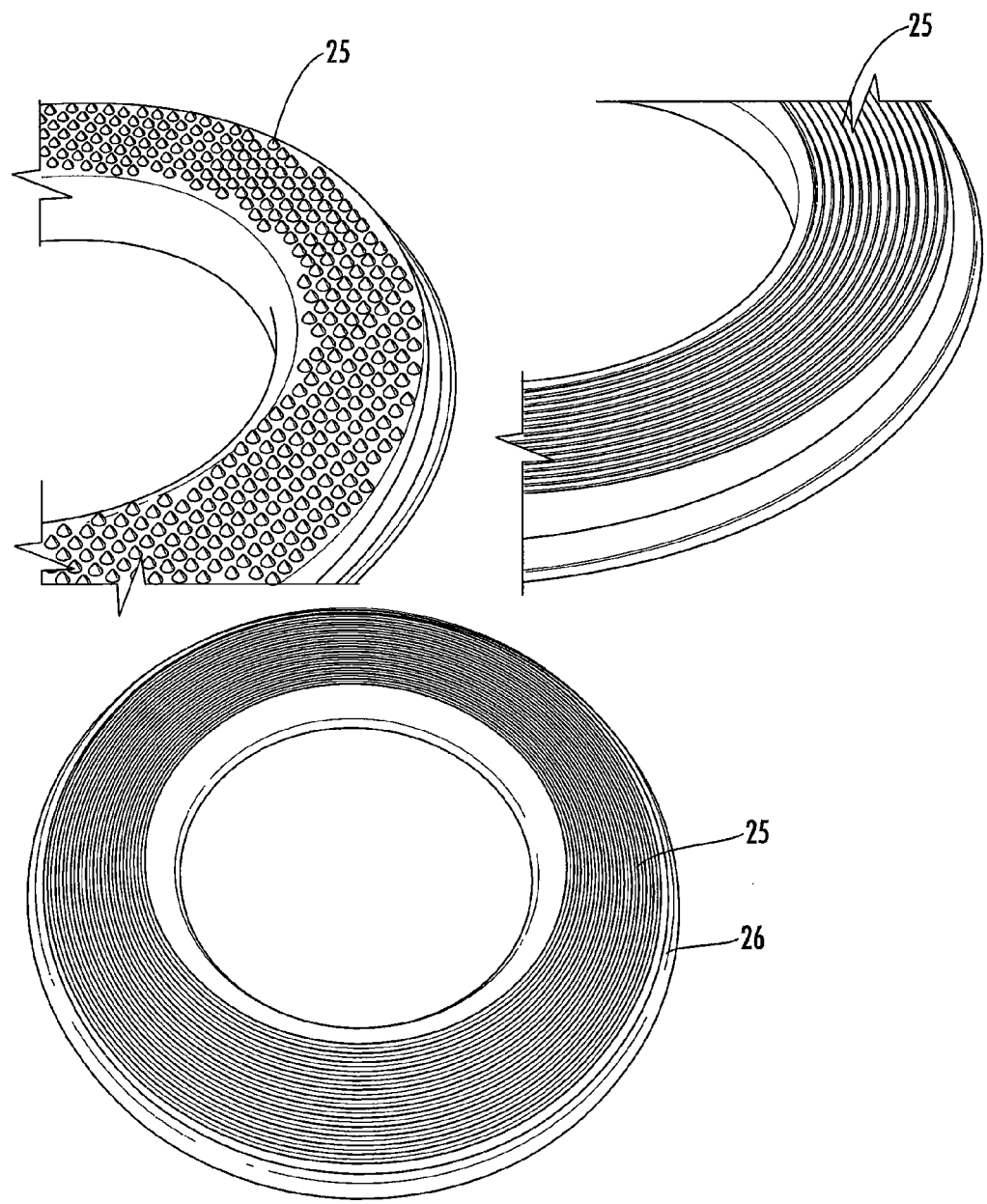
FIG. 9 presents photographs of bottom views of perimeter members according to some embodiment having other examples of friction surfaces: knurl-like, and rough (concentric circles). In the bottom panel, the perimeter member has an O-ring in a ridge at its outer edge.

While the tissue segment is being stretched, the ends of the segment are held in place in the tissue culture by the friction from the friction surface of the perimeter member (25) as held onto the tissue by the attachment of the top solid support (20) onto the bottom solid support (10). As seen in FIG. 8 and FIG. 9, the friction surface of the perimeter member (25) may be provided as a patterned surface. The outer edge of the perimeter member (25) may be configured to receive one or more O-rings (26) or other means of sealing liquid such as the media provided in the reservoir (30). Many different patterns may be used, and those shown are but exemplary patterns. Any surface that can be used to provide friction sufficient to hold the outer portion of the tissue in place can be used. For maximum stretching efficiency, the friction patterns should be substantially uniform around the friction surface in contact with the tissue.

Though in currently preferred embodiments the tissue is orbicularly expanded out from a device having a circular or substantially circular opening in the top portion thereof (top solid support (20) and perimeter member (25)), other shapes are contemplated. For example, the opening may be oval or substantially oval, square, rectangular, etc. However, the shape is optimally chosen to exert a more evenly-distributed force throughout the tissue during expansion.

As an alternative, the top solid support (20) and perimeter member (25) may be provided as a unitary member rather than as separate pieces.

Figure 10:
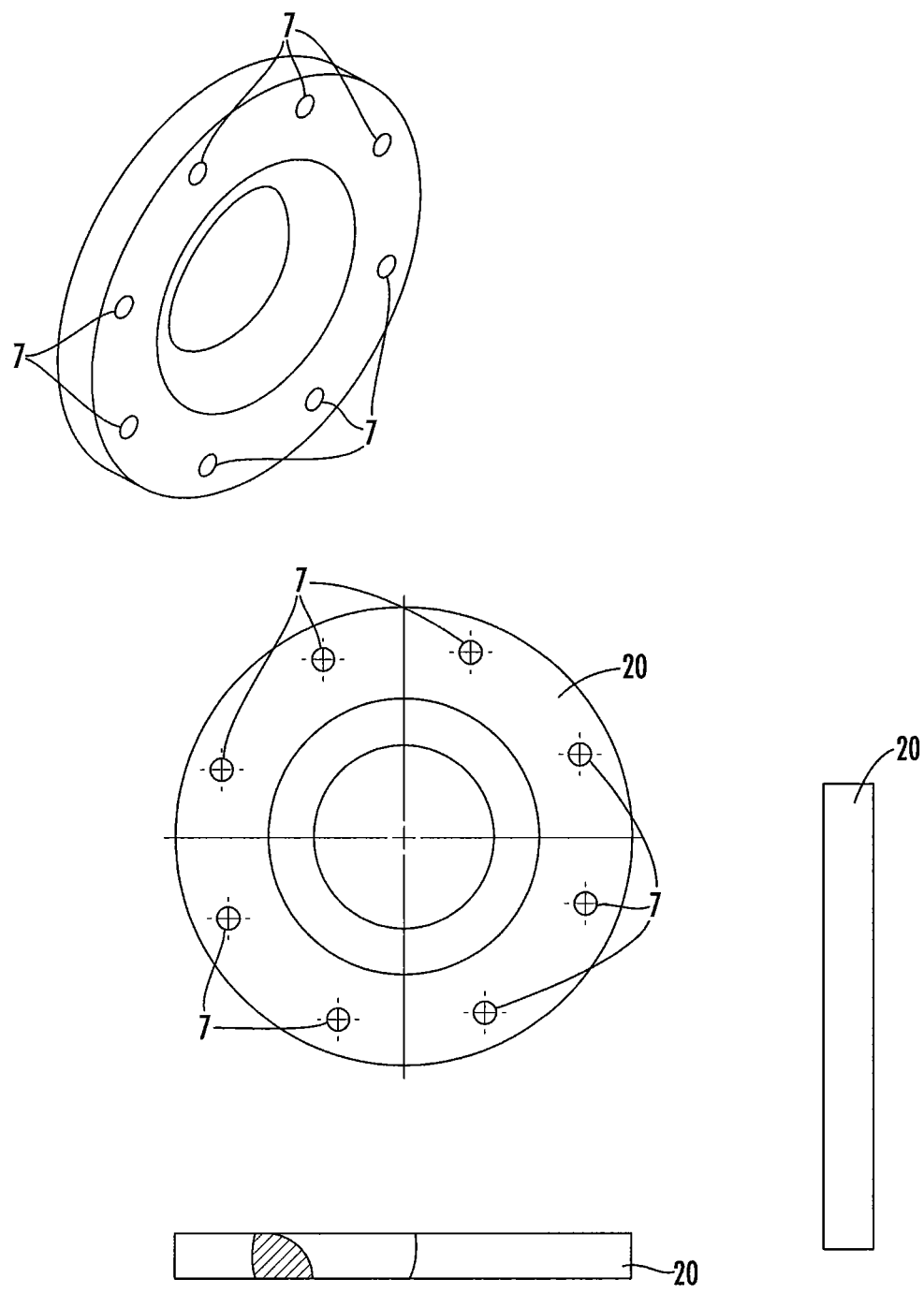
FIG. 10 is a schematic drawing of a top solid support according to some embodiments. The inner edge of the support may be rounded to minimize the risk of sharp edges coming into contact with the expanding tissue.
Figure 11:
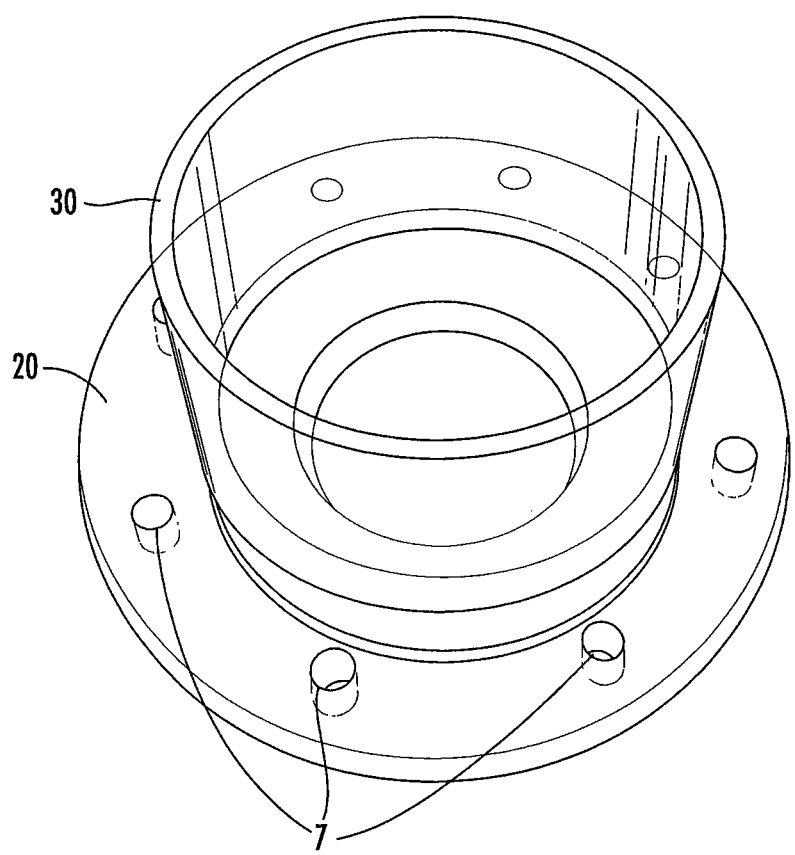
FIG. 11 shows a photograph of a top perspective view of the top solid support having a media reservoir according to some embodiments.
Figure 12:
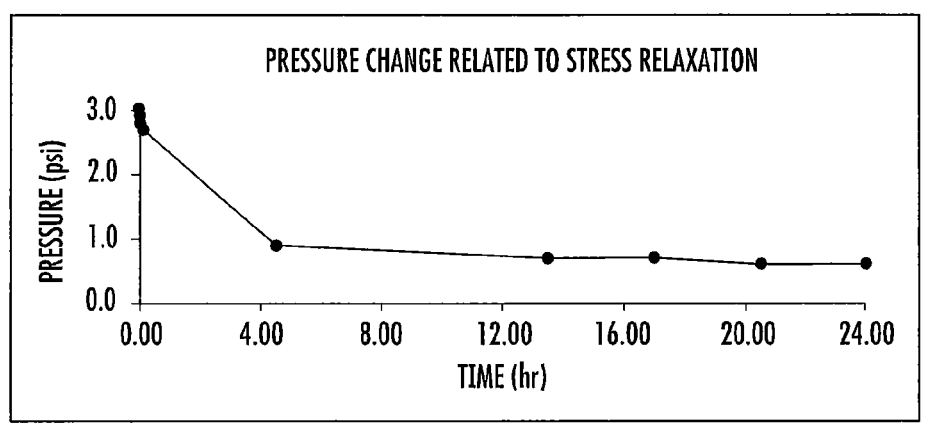
FIG. 12 shows the results of a 24-hour stress relaxation test of porcine skin in an orbicular expander.

The top solid support (20) and/or perimeter member (25) may have rounded edges in the inner perimeter thereof to minimize tissue damage during the orbicular expansion, as shown in FIG. 10 and FIG. 11.

Figure 14:
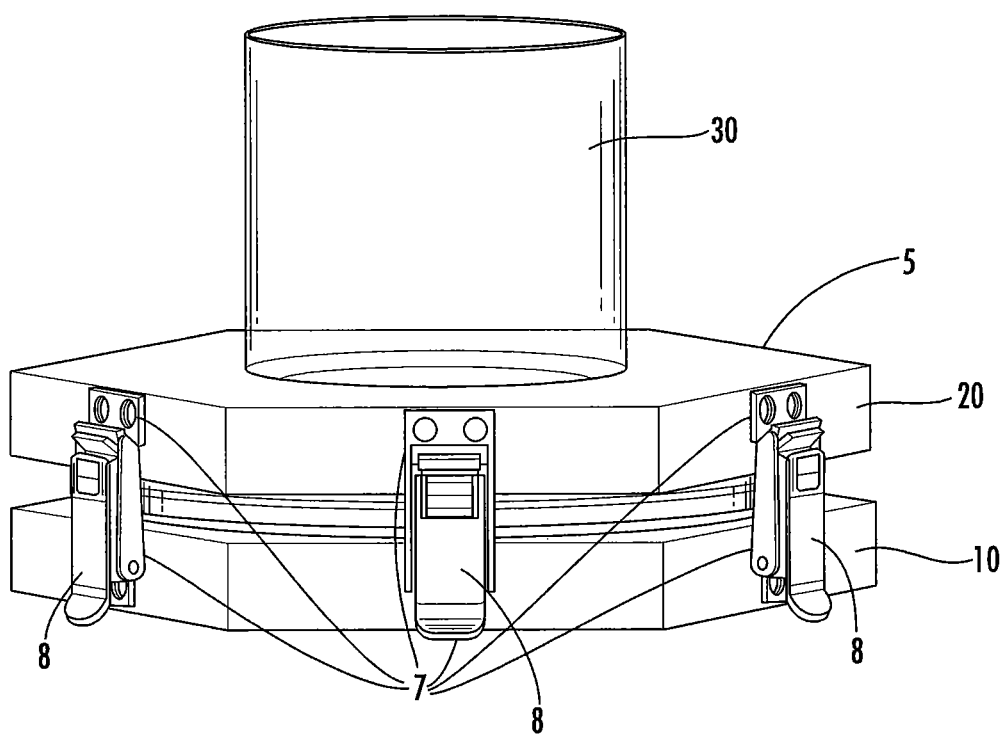
FIG. 14 presents an assembled view of an orbicular expander device according to some embodiments where the top solid support and bottom solid support are provided in a hexagonal shape with clamps.
Figure 15:
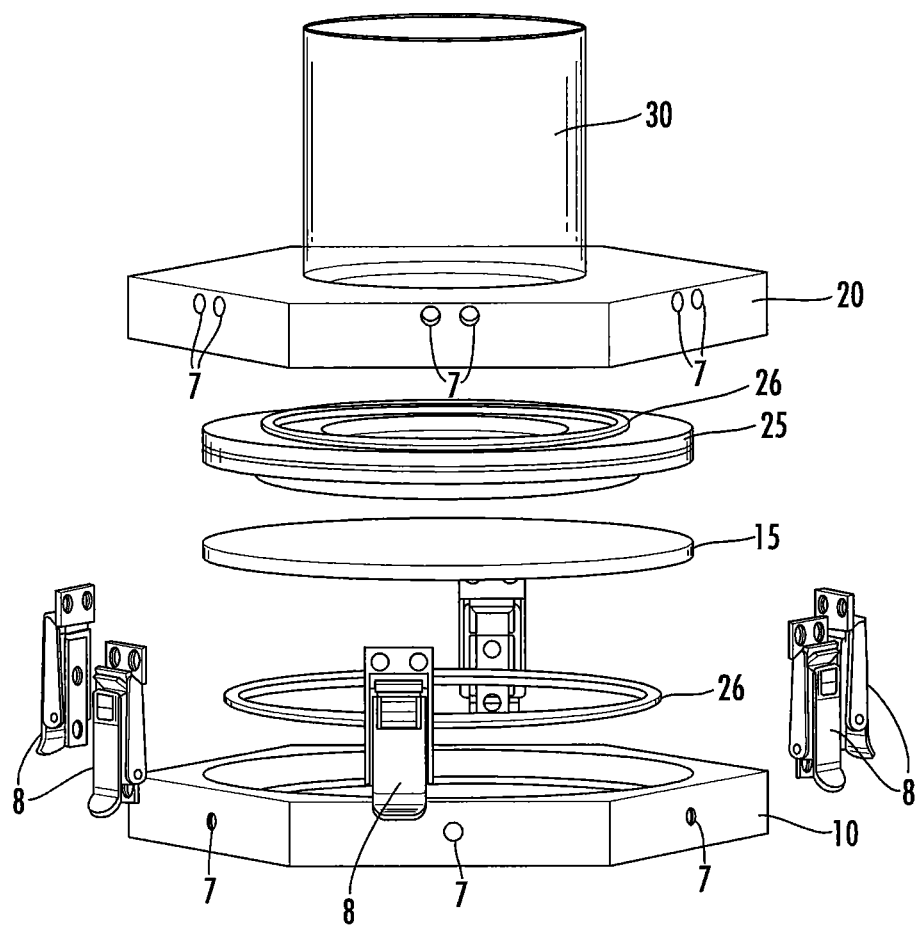
FIG. 15 presents an exploded perspective view of an orbicular expander device according to some embodiments.

As illustrated in FIG. 14 and FIG. 15, in some embodiments a device (5) includes a bottom solid support (10) and a top solid support (20) each provided in a hexagonal shape. The points of attachment (7) are configured to receive clamps (8) as the attachment members.

As shown in FIG. 16 and FIG. 17, in some embodiments the perimeter member (25) may be assembled from three pieces. Shown are pins (27) configured to pierce the tissue (13) situated between a top piece (25a) and bottom piece (25b) of the perimeter member (25). An o-ring (26) is provided between the perimeter member (25) and the expandable membrane (15) and surrounding, but in some embodiments not touching, the tissue (13). In this embodiment, the tissue is secured by the pins (27) and the o-ring (26) between the perimeter member (25) and the expandable membrane (15) reduces or prevents the tissue (13) from being compressed by the perimeter member (25) onto the expandable membrane (15) and/or reduces or prevents the pins (27) from puncturing the expandable membrane (15). During assembly, the tissue (13) may be placed over all pins (27) and pressed down such that all the pins puncture through tissue edges to hold it in place.

In the device (5) shown in FIG. 16 and FIG. 17, the pins (27) puncture through the tissue (13) from top to bottom. However, it is also contemplated that the device (5) may be provided in which the pins (27) puncture through the tissue (13) from bottom to top, in which the tissue (13) is situated between the perimeter member (25) and the top solid support (20).

The force applied to stretch the tissue is supplied by fluid pressure under the expandable membrane (15), which can be either static or dynamic. The amount of force applied to the tissue is minimally that required to cause the tissue to stretch or expand. "Stretch" or "expand" refers to the increase in length and/or area of the tissue along at least one axis, and preferably according to some embodiments along two axes and/or a three dimensional area, in response to an applied force. Since the strength of different tissue segments obtained from the same donor may vary, the forces may best be determined empirically by the amount of tissue stretch that is obtained. A typical stretched skin segment has an area after being subjected to stretching forces (over an appropriate length of time) that is at least twice that of the skin segment prior to being subjected to the stretching forces. For human skin, stretching of at least 2% per day is desired, preferably at least 5%, more preferably at least 10%. Non-human skin can be either more or less elastic than human skin and thus may be stretched correspondingly less or more than these amounts.

In some embodiments, tissue can be stretched until rupture or cell death induced by the strain of stretching, which can readily be followed by histological examination. In some cases, it may be desirable to keep stretching under 40 or 50% per day to avoid physical tissue damage such as tearing and/or disruption of tissue matrices. However, some reports state that stretch up to 40% can stimulate skin cells to improve cell survival and matrix secretion. In some embodiments, tissue can be monitored for signs of the initiation of tearing (e.g., fracture lines) and the stretching forces modified accordingly to allow the skin to heal and recover. Thus, in some embodiments the flexible membrane (15) is transparent, and the tissue may be illuminated from the bottom of the device with a light source (not shown) to allow better visual monitoring of the tissue for signs of tearing.

The foregoing configuration advantageously provides orbicular expansion of a tissue. Numerous other configurations can also be used to expand tissue in a similar manner. While a device having a top solid support and a bottom solid support is currently preferred, other embodiments may be used by those skilled in the art without departing from the general teachings herein of orbicular tissue expansion and devices therefor.

As noted, though in some embodiments the device is used to stretch skin, the device is also useful for stretching and/or conditioning and/or culturing other organized tissues, for example, muscle such as skeletal muscle, smooth muscle (e.g., bladder tissue), etc. In addition, the device may be used to condition scaffolds or supports seeded with cells to create a desired tissue.

"Skin cells" include those cells normally found in skin, and include epidermal cells (e.g., keratinocytes, melanocytes, Merkel cells, Langerhan cells, etc., and any combination thereof) and dermal cells (e.g., fibroblasts, adipocytes, mast cells, macrophages, and any combination thereof). Skin tissue produced by the process of the present invention is useful for grafting onto or implantation into a subject to, for example, treat burns and other wounds such as incisions, lacerations, and crush injuries (e.g., postsurgical wounds, and posttraumatic wounds, venous leg ulcers, diabetic foot ulcers, etc.); or for use in plastic surgery and/or tissue reconstruction.

"Muscle cells" include those cells normally found in muscle tissue, including smooth muscle cells, cardiac muscle cells, skeletal muscle cells, and any combination thereof. Muscle cells/tissues produced by the processes described herein are useful for, among other things, implantation into a subject to treat muscle injuries or defects, and/or promote muscle healing.

Precursor or stem cells may also be used to seed supports and appropriately stimulated to differentiate into cells of interest (e.g., skin or muscle cells). "Supports" on which cells may be seeded and grown to produce cultured tissue of the present invention include any suitable support. See, e.g., U.S. Pat. Nos. 6,998,418; 6,485,723; 6,206,931; 6,051,750; and 5,573,784. Collagen supports or decellularized tissue supports may be used. The length of stretching of the solid support may be to a dimension at least 5% greater in length than the static position, and the relaxing may comprise retracting the support to a dimension not greater in length than the static position. In some embodiments, the "static position" may be intermediate between the stretched and relaxed position, and in such cases the relaxing may comprise retracting the support to a dimension at least 5% lesser in length than the static position.

The present disclosure is further illustrated by the following non-limiting examples.

EXAMPLES

Example 1: Preliminary Testing

Several preliminary tests were conducted to validate the design of the skin stretching bioreactor. FIG. 10 presents the results of a 24-hour stress relaxation test of porcine skin in the orbicular expander. Initially pressurized to 3.0 psi, the pressure started to drop in the first minute and leveled off at 0.6 psi, 20% of the initial pressure.

Table 1 shows the results of testing different friction surfaces on the perimeter member of the device. The clamping force is the force applied downward on the skin to generate friction. The larger the clamping force, the larger the friction and resistance to slipping. If the clamping force is too high, significant stress concentrations may develop at the clamping site.

At lower clamping forces, several samples slipped at the gripping surface. However, failures in the skin were obtained at sites other than the clamping site using three different friction surfaces (knurl-like, pin, rough (series of concentric circles)).

While some of the lower clamping force experiments in Table 1 did result in slipping, the higher clamping force experiments did not appear to generate significant stress concentrations at the friction surfaces, as those samples tore in the expanded area, well away from the friction surfaces. Therefore, the higher clamping forces are acceptable.

TABLE 1

Preliminary Test Data to Failure

| Friction Surface | Clamping Force (lbs) | Loading | Maximum Pressure at Failure (lbs) | Failure Mode |
| --- | --- | --- | --- | --- |
| Knurl-like | 88.87 | Non-Cyclic | 4.0 | Sample Slipped at Gripping Surface |
| Knurl-like | 129.44 | Non-Cyclic | 7.0 | Sample Tore |
| Knurl-like | 129.44 | Cyclic | 12.2 | Sample Tore |
| Pin | 88.87 | Non-Cyclic | 1.0 | Sample Slipped at Gripping Surface |
| Pin | 129.44 | Non-Cyclic | 7.0 | Sample Tore |
| Pin | 88.87 | Cyclic | 8.0 | Sample Tore |
| Rough | 129.44 | Non-Cyclic | 9.6 | Sample Tore |

Skin is naturally expanded by the body through a number of life events such as growth, pregnancy, and weight gain. In vivo stretching used during reconstructive surgeries may be done in advance by inserting a balloon like device under the skin in the area that is slowly inflated by addition of a liquid. The skin is slowly stretched and grows due to the forces created by the inflated balloon.

Thus it is hypothesized that the use of a pressurized bioreactor design for orbicular expansion as taught herein will provide the same or more stretching with less skin tearing than other methods of in vitro stretching.

The proposed bioreactor is also designed to more evenly distribute pressure on the skin and reduce the skin tearing around the clamping mechanisms, which are provided by a perimeter member having a friction surface that does not unduly place pressure on the points of tissue attachment to the device.

Figure 13:
FIG. 13 shows photographs of orbicularly expanded skin tearing at sites within the tissue sample, as opposed to at the site of attachment to the device.

Preliminary testing of the orbicular expander capability has revealed that clamped skin will fail at locations away from the clamp site, as shown in the images in FIG. 13. This is a significant step forward when compared to the premature, clamping-related failures of biaxial expansion. High-pressure induced failures of skin specimens in the orbicular expander device demonstrate that the device can achieve the ultimate stress of skin and maximum expansion, as opposed to biaxial systems which fail at attachment points with much lower stresses and strains.

Example 2: Further Testing

The device uses a biocompatible flexible, expandable membrane to produce pressure on the skin. The two halves of the base unit are clamped together using the 8 bolts, and the expandable membrane and skin patch are sandwiched in between and sealed by two O-rings, with the epidermal side of the skin facing the flexible membrane. A syringe pump is used to inject fluid into the base of the device under the expandable membrane and cause the membrane to expand in an orbicular manner. A pressure or volume detector/controller provides a measurement of the force being applied, and the pressure is adjusted as desired.

On the top of the base unit is a container filled with media to provide nutrients to the dermis and keep the tissue hydrated. The expandable membrane can be inflated using an external pump, and a pressure sensor will monitor the expansion pressure. The expandable membrane will mimic the forces of inflatable balloons that are used in vivo, but will push on the epidermal side rather than the dermal side. Due to the thickness of the skin patches, only the epidermis and the dermis layers are present, which results in a porous tissue sample. When inflatable balloons are used in vivo, they are placed under the entire thickness of the skin and are, therefore, not putting pressure directly on to the cells in the dermis layer.

A reason for not using the full thickness of the skin is that the healing of the donor site would be very difficult. The stem cells present in the hypodermis layer plays a critical role in regenerating the skin at the donor site.

Example 3: Three Pilot Tests

Three tests (Samples, 1, 2 and 3) were conducted using the circular device design to verify the LabView program/software and syringe pump functions, and demonstrate proof of concept of orbicular skin expansion. In conducting the first two tests (Samples 1 and 2), fluid volume for dome expansion was the controlled parameter while pressure and time were the recorded variables. In sample 3 test, pressure for dome expansion was the controlled parameter, and the intent was to determine the longest length of time the skin remained in the bioreactor under some pressure without tearing (goal was 48 hours). After 48 hours the skin still remained intact with no contamination, so the test was continued for a total of 55 hrs, after which the sample was contaminated. Details of each test were as follows:

Sample 1

The skin was prepared and loaded into the bioreactor using the compression knurled insert to clamp the skin. The goal was to test the newly-built syringe pump as well as validate the digital pressure sensor for correlation with the analog pressure sensor connected in the system. Fluid (volume) was pumped into the system 0.5 mL at a time, while time and pressure were observed and recorded. When the pressure remained constant after three to four 0.5 mL inputs, the skin was left to relax for some time, until the pressure gradually lowered. This was continued until the sample tore. To measure expansion, the inner diameter of the clamping insert was used for initial surface area; a diameter of 5.08 cm translated to 20.27 cm$^2$ area. The final surface area after expansion was measured using the similar principle; when the skin is unloaded from the knurled clamping insert, a clear impression from the ring is left of the skin, and the new diameter of the skin can be measured. The final diameter was 5.6 cm equaling a total area of 24.63 cm$^2$ concluding a 22% increase in area of expanded skin.

Sample 2

Sample 2 was prepared and loaded similar to Sample 1. Using the information learned in Sample 1 test, the volume inputs were more controlled and allowed for more time between inputs. The experiment was concluded when the sample tore. The expansion was measured in the same way as sample 1 with an initial surface area of 20.27 cm$^2$ and final area of 26.42 cm$^2$, a 30% increase.

Sample 3

The skin was prepared the same as Sample 1 and 2. However the pin insert was used for clamping instead of knurled insert. The insert was turned upside down and pushed down to puncture the skin around the edges and hold it. This test was concluded after 55 hours of testing with no tears. When using the pin insert, the initial diameter of the skin is same as the diameter of the pin ring (6.096 cm) and the resulting area is 29.19 cm$^2$. The final diameter/area was measured from the puncture holes left behind in the skin after expansion. Sample 3 was measured to have a final diameter of 6.4 cm resulting in a total area of 32.17 cm$^2$. While this experiment did not result in any leaks at the pin punctures, the skin loading procedure resulted in contamination in later experiments. Therefore, for future testing the pin design was changed so that the pins do not directly puncture the polymer membrane at the start of the experiment. The skin is loaded on the pins first (epidermis up) so that when it is flipped over and placed into the hexagon orbicular expander, the epidermis faces down.

TABLE 2

Pilot Tests

| Test | Percentage increase | Expansion Time (hrs) | Maximum Pressure (psi) | Tear | Observations |
|---|---|---|---|---|---|
| Sample 1 | 22% | 16 | 9 | Yes | keep volume constant until skin relaxes and pressure begins to lower |
| Sample 2 | 30% | 18 | 6 | Yes | after initial expansions give skin more time between inputs of volume to allow repair |
| Sample 3 | 10% | 55 | 2.5 | No | skin can survive over 48 hours at very low pressures and continue to show expansion |

The foregoing is illustrative of the present invention, and is not to be construed as limiting thereof. The invention is defined by the following claims, with equivalents of the claims to be included therein.

That which is claimed is:

1. A tissue stretching device comprising:
  a bottom solid support comprising a fluid chamber therein, said fluid chamber having a fluid inlet and fluid outlet;
  an expandable membrane attached to said bottom solid support and configured to be in fluid communication with a fluid in said chamber, wherein said expandable membrane is configured to undergo orbicular expansion in the presence of fluid pressure in said chamber;
  a top solid support having a substantially circular opening therein;
  a perimeter member further defining said substantially circular opening of said top solid support and configured to hold edges of a tissue onto the expandable membrane during the orbicular expansion of the center of the tissue;

wherein the bottom solid support is configured to attach to the top solid support, and wherein said expandable membrane and said perimeter member are situated between said bottom solid support and said top solid support.

2. The device of claim 1, wherein said perimeter member comprises a friction surface to hold the tissue onto the expandable membrane during the expansion.

3. The device of claim 1, wherein said perimeter member comprises protrusions sized to puncture and/or penetrate the tissue to hold the tissue onto the expandable membrane during the expansion.

4. The device of claim 1, wherein said expandable membrane comprises an expandable polymer.

5. The device of claim 1, wherein said top solid support further comprises a chamber configured to hold media, said media in fluid communication with a tissue being stretched in said device.

6. The device of claim 1, wherein said perimeter member comprises one or more O-rings to provide a fluid seal between said perimeter member and said top solid support.

7. The device of claim 1, wherein the device is configured to stretch skin tissue.

8. The device of claim 1, wherein opening of said perimeter member is circular and has a diameter of from 1 to 20 centimeters.

9. The device of claim 1, wherein the opening of said perimeter member is circular and has a diameter of from 5 to 15 centimeters.

10. The device of claim 2, wherein the friction surface of said perimeter member comprises a rough pattern.

11. The device of claim 1, wherein said device further comprises a pressure detector and/or controller operatively associated with the fluid of said fluid chamber.

12. The device of claim 11, wherein the pressure detector and/or controller is configured to regulate pressure applied to the tissue by the expandable membrane.

13. A method of orbicularly stretching a tissue comprising:

attaching the tissue into the device of claim 1; and stretching the tissue with the device, to thereby orbicularly stretch the tissue.

14. The method of claim 13, wherein the tissue is skin tissue.

15. The method of claim 14, wherein said skin tissue comprises an epidermal tissue layer and a dermal tissue layer, and wherein said skin tissue has an epidermal surface and a dermal surface.

16. The method of claim 15, wherein said attaching is carried out by placing the skin tissue with the epidermal surface in direct contact with said expandable membrane, and overlaying said tissue with the perimeter member on the dermal surface.

17. The method of claim 16, wherein the stretching is carried out over a time of from 1 hour to 1 or 2 weeks.

18. The method of claim 13, wherein the stretching comprises applying a fluid pressure of from 1 to 10 psi to said tissue.

19. A method of treating a skin wound on a subject in need thereof, comprising:

providing a skin tissue harvested from a donor;

stretching the skin tissue with the device of claim 1 to form an orbicularly stretched skin tissue; and then grafting the orbicularly stretched skin tissue onto said subject, to thereby treat the skin wound.

20. The method of claim 19, wherein the skin tissue is autologous.

* * * * *